US006772091B1

(12) United States Patent
Roberts

(10) Patent No.: US 6,772,091 B1
(45) Date of Patent: Aug. 3, 2004

(54) DETERMINING THE DEPTH OF REINFORCING BARS IN A CONCRETE STRUCTURE USING ELECTROMAGNETIC SIGNALS

(75) Inventor: Roger L. Roberts, Amesbury, MA (US)

(73) Assignee: Geophysical Survey Systems, Inc., North Salem, NH (US)

( * ) Notice: Subject to any disclaimer, the term of this patent is extended or adjusted under 35 U.S.C. 154(b) by 0 days.

(21) Appl. No.: 09/457,512

(22) Filed: Dec. 8, 1999

Related U.S. Application Data

(60) Provisional application No. 60/111,415, filed on Dec. 8, 1998, now abandoned.

(51) Int. Cl.[7] ................................................ G01B 7/26
(52) U.S. Cl. ........................ 702/166; 324/644; 342/118
(58) Field of Search ......................... 702/166, 79, 170; 342/22, 118; 324/644, 635, 637, 645; 73/597, 602, 620

(56) References Cited

U.S. PATENT DOCUMENTS

| | | | |
|---|---|---|---|
| 3,665,466 A | | 5/1972 | Hibbard |
| 4,698,634 A | | 10/1987 | Alongi et al. ................. 342/22 |
| 4,837,509 A | * | 6/1989 | Dodmann et al. .......... 324/207 |
| 5,130,711 A | | 7/1992 | Kimura et al. |
| 5,384,715 A | | 1/1995 | Lytton ......................... 364/550 |
| 5,420,589 A | | 5/1995 | Wells et al. |
| 5,748,003 A | | 5/1998 | Zoughi et al. ............... 324/644 |
| 5,835,053 A | * | 11/1998 | Davis ........................... 342/22 |
| 5,835,054 A | | 11/1998 | Warhus et al. |
| 5,905,455 A | * | 5/1999 | Heger et al. .................. 342/22 |
| 5,939,889 A | | 8/1999 | Zoughi et al. .............. 324/643 |
| 5,952,561 A | | 9/1999 | Jaselskis et al. ................. 73/78 |
| 5,986,602 A | * | 11/1999 | Frink .......................... 342/126 |
| 6,029,521 A | * | 2/2000 | Lin et al. ...................... 73/597 |
| 6,198,293 B1 | * | 3/2001 | Woskov et al. ............. 324/637 |

OTHER PUBLICATIONS

R. Zoughi, G. L. Cone, and P.S. Nowak, "Microwave Nondestructive Detection of Rebars in Concrete Slabs," NDT Solution, 1991, The American Society for Nondestructive Training, Inc.

* cited by examiner

Primary Examiner—Marc S. Hoff
Assistant Examiner—Paul Kim
(74) Attorney, Agent, or Firm—Wolf, Greenfield & Sacks, P.C.

(57) ABSTRACT

Ground penetrating radar (GPR) is a technique that may be used to image the inside of a structure by collecting the echoes (or reflections) resulting from electromagnetic signals such as, for example, electromagnetic waves of typically high frequency, being radiated into the structure. Typically, the rebars inside a reinforced concrete structure are strong radar wave reflectors. Locating rebars within a reinforced concrete structure and determining their depths may be accomplished by analyzing the reflections, particularly the amplitudes and arrival times of the reflections, from the rebars in the reinforced concrete structure. Provided is a method and system for determining, for a substantially concrete structure having at least a first side and containing one or more reinforcing bars, a distance of the one or more reinforcing bars from the first side of the substantially concrete structure. One or more computer-readable data signals are received, and each data signal represents an electromagnetic signal detected from an area of the concrete structure. One or more of the detected electromagnetic signals include electromagnetic energy reflected from the concrete structure as a result of an electromagnetic signal transmitted into the concrete structure. A distance of one or more of the reinforcing bars from the first side of the substantially concrete structure is determined from the one or more computer-readable data signals.

87 Claims, 8 Drawing Sheets

DETERMINING THE DEPTH OF REINFORCING BARS IN A CONCRETE STRUCTURE USING ELECTROMAGNETIC SIGNALS

This application claims priority to provisional application serial No. 60/111,415, filed Dec. 8, 1998, entitled CONCRETE COVER ASSESSMENT TECHNIQUE FOR NEW BRIDGE DECKS, and now abandoned.

FIELD OF INVENTION

This invention relates to locating metallic objects in an inhomogeneous structure. More particularly, this invention relates to a system and method for accurately determining the depths of reinforcing bars of a reinforced concrete structure such as, for example, a bridge deck, using electromagnetic signals.

BACKGROUND OF INVENTION

A bridge deck is the portion of a bridge upon which vehicles travel. Bridge decks are typically made of reinforced concrete. As referred to herein, concrete is a mixture of fine and coarse aggregates such as, for example, crushed stone or gravel, firmly bound into a monolithic mass by a cementing agent such as, for example, Portland cement. Reinforced concrete as referred to herein is concrete in which metal rods or bars, preferably made of steel, are incorporated into the concrete in such a manner as to reinforce or strengthen the more or less brittle nature of concrete and the resulting structure. Such rods or bars carry the tension to which a concrete structure may be subjected, thus reinforcing the concrete, and are referred to herein as reinforcing bars or rebars. As used herein, a substantially concrete structure is a structure where the primary constituent is concrete. Such a substantially concrete structure may contain reinforcing bars to improve tensile strength, a waterproofing membrane to protect the structure from moisture, an asphalt layer or overlay, other added elements to improve durability or performance, and possible inadvertently added elements.

The depth of the rebars relative to the concrete surface, commonly called "concrete cover," is important for at least two reasons. First, the depth of the rebar affects the overall tensile strength of the bridge deck, and second, rebar corrosion potential is related to the depth of the rebar in the concrete. Rebar corrosion may compromise the structural integrity of a reinforced concrete bridge deck, and lead to further deterioration of the concrete that further compromises structural integrity. Further, a bridge deck may be subjected to extreme climates such as, for example, snow, ice, and thermal freeze-thaw cycles. Further, such extreme climates, and human intervention to permit the flow of traffic on the bridge amidst these harsh conditions, may result in the ingress of road salt. These factors may lead to the eventual deterioration of portions of the bridge deck, making travel on the bridge unsafe.

Consequently, the State of New Hampshire, USA, has implemented a quality control (QC) policy which rewards bridge contractors who place the rebars at the correct depth in new bridge decks, and penalizes contractors negligent in rebar placement. The QC policy specifies the measurement of rebar cover to within ±3 millimeters. The policy also requires the measurement of many rebars per bridge deck, to establish a statistical basis for assessing contractor performance. The large number of rebars that need to be located makes prohibitive the use of invasive techniques, such as, for example, core drilling, to obtain the depths of all of the rebars.

Thus, there is an established need to accurately determine the depth of rebars used in the construction of reinforced concrete bridge decks.

SUMMARY OF THE INVENTION

Ground penetrating radar (GPR) is a technique that may be used to image the inside of a structure by collecting the echoes (or reflections) resulting from electromagnetic signals such as, for example, electromagnetic waves of typically high frequency, being radiated into the structure. Typically, the rebars inside a reinforced concrete structure are strong radar wave reflectors. Locating rebars within a reinforced concrete structure and determining their depths may be accomplished by analyzing the reflections, particularly the amplitudes and arrival times of the reflections, from the rebars in the reinforced concrete structure.

In an embodiment, provided is a method of determining, for a substantially concrete structure having at least a first side and containing one or more reinforcing bars, a distance of the one or more reinforcing bars from the first side of the substantially concrete structure. One or more computer-readable data signals are received, and each data signal represents an electromagnetic signal detected from an area of the concrete structure. One or more of the detected electromagnetic signals include electromagnetic energy reflected from the concrete structure as a result of an electromagnetic signal transmitted into the concrete structure. A distance of one or more of the reinforcing bars from the first side of the substantially concrete structure is determined from the one or more computer-readable data signals.

In another embodiment, for a substantially concrete structure having at least a first side and containing one or more reinforcing bars, a system for determining a distance of the one or more reinforcing bars from the first side of the substantially concrete structure is provided. The system includes means for receiving one or more computer-readable data signals, wherein each data signal represents an electromagnetic signal detected from an area within the concrete structure, and wherein one or more of the detected electromagnetic signals include electromagnetic energy reflected from the concrete structure as a result of an electromagnetic signal transmitted into the concrete structure. The system further includes means for determining from the one or more computer-readable data signals a distance of one or more of the reinforcing bars from the first side of the substantially concrete structure.

In an aspect of this embodiment, the means for determining includes means for selecting one or more of the data signals, each selected data signal corresponding to a reinforcing bar, and means for determining, for each selected signal, a first distance of the corresponding reinforcing bar from the first side of the substantially concrete structure.

In another aspect of this embodiment, each data signal represents an electromagnetic signal detected over a detection period of time, and the means for determining the first distance for each selected signal includes means for determining, for each selected signal, a portion of the selected signal during which the electromagnetic signal represents electromagnetic energy reflected from a corresponding reinforcing bar. The means for determining the first distance further includes means for determining, for each data signal, the first distance of the corresponding reinforcing bar from the first side from the determined portion of the selected signal.

In another aspect of this embodiment, the system further comprises means for determining a velocity value representing a velocity of each electromagnetic signal in concrete of the substantially concrete structure. The means for determining the first distance includes means for determining, for each selected signal, a first point in time during the detection period corresponding to a peak amplitude of the selected signal and means for calculating, for each selected signal, the first distance using the velocity value and the first point in time.

In yet another aspect of this embodiment, for each selected signal, the means for determining the first distance further includes means for determining a second point in time corresponding to a peak amplitude of electromagnetic energy reflected from the first side of the substantially concrete structure, means for subtracting the first point in time from the second point in time to produce a propagation time within the concrete structure by the detected signal and means for calculating the first distance using the velocity value and the propagation time.

In yet another aspect of this embodiment, the transmitted signals were transmitted from a first antenna and the detected signals were detected by a second antenna located a second distance from the first antenna. For each selected signal, the means for calculating the first distance includes means for applying an equation:

$$d = \frac{1}{2}\sqrt{v^2 t^2 - a^2},$$

wherein d is the first distance, t is the propagation time, v is the velocity value, and a is the second distance.

In another aspect of this embodiment, the means for determining the first distance includes means for receiving a second distance value indicative of a distance measured from the first side of the concrete structure to one of the one or more reinforcing bars and means for calculating the velocity value from the second distance value.

In another aspect of this embodiment, the transmitted signals were transmitted from a first antenna and the detected signals were detected by a second antenna located a third distance from the first antenna. For each selected signal, the means for determining the first distance includes means for determining a propagation time of the detected signal in the substantially concrete structure, and wherein the means for calculating the velocity value includes means for applying an equation:

$$v = \frac{2}{t}\sqrt{(a/2)^2 + d^2},$$

wherein v is the velocity value, a is the third distance, t is the propagation time and d is the second distance.

In yet another aspect of this embodiment, each transmitted electromagnetic signal was transmitted at a different position along the first side of the concrete structure, and the means for determining the first distance for each selected signal further includes means for determining, for each data signal, a peak amplitude of the data signal during the determined portion. The means for selecting a data signal includes, for one or more spatial intervals of a first length along the first side of the substantially concrete structure, means for selecting a data signal with a peak amplitude of a highest magnitude from among data signals corresponding to electromagnetic signals transmitted within the spatial interval.

In another aspect of this embodiment, the system further comprises means for migrating the data signals to facilitate selecting the data signal with a peak amplitude of the highest magnitude.

In another aspect of this embodiment, the transmitted signals were transmitted from a first antenna and the detected signals were detected by a second antenna located a second distance from the first antenna, the second distance having a midpoint on an imaginary straight between the first and second antennas, and an amplitude of each data signal is directly related to a distance between the area corresponding to the data signal and the midpoint of the second distance.

In yet another aspect of this embodiment, each of the data signals represent an electromagnetic signal detected at a point along a substantially straight line along a first dimension of the first side of the concrete structure, and each detected electromagnetic signal is detected over a period of time. The system further comprises means for displaying a graph of one or more of the data signals, a first axis of the graph representing time of detection, a second axis of the graph representing a distance along the first dimension, the means for displaying including means for representing an amplitude of each of the one or more data signals over the detection time, the location, with respect to the second axis, of each represented data signal corresponding to the point at which the signal was detected.

In another aspect of this embodiment, the means for selecting the data signals includes means for selecting each data signal from the graph in accordance with the amplitudes of the represented data signals.

In another aspect of this embodiment, the means for determining includes means for adjusting the data signals by removing from each data signal data representing electromagnetic signals not reflected from the substantially concrete structure, and means for determining the depth of one or more reinforcing bars of the substantially concrete structure from the adjusted data.

In another embodiment, for a substantially concrete structure having at least a first side and containing one or more reinforcing bars, a system for determining a distance of the one or more reinforcing bars from the first side of the substantially concrete structure is provided. The system includes a computer-readable storage mediun to store one or more computer-readable data signals, wherein each data signal represents an electromagnetic signal detected from the concrete structure, and one or more of the detected electromagnetic signals include electromagnetic energy reflected from the concrete structure as a result of an electromagnetic signal transmitted into the concrete structure, and wherein each detected signal corresponds to an area within the concrete structure. The system also includes a data analysis application 300 to receive the computer-readable data signals and determine from the data signals a distance of one or more of the reinforcing bars from the first side of the substantially concrete structure.

These and other features and advantages of the invention will be more readily understood and appreciated from the detailed description below, which should be read together with the accompanying drawing figures.

DETAILED DESCRIPTION

The following description is merely illustrative and not limiting, and is presented by way of example only. Thus, although the following describes an embodiment of determining the depth of rebars in a concrete structure, using a reinforced concrete bridge deck as an example, the system and method described herein may be applied to other inhomogeneous structures, particularly concrete structures, containing an electromagnetically reflective material such as, for example, metal. Further, although the following describes an embodiment using a concrete structure, the system and method described herein may be applied to structures made from other materials having loosely similar electrical properties (e.g., permittivity) and physical properties to concrete.

Several models of the Subsurface Interface Radar (SIR®) System available from Geophysical Survey Systems, Inc. (GSSI), North Salem, New Hampshire, are suitable commercial GPR systems for use in determining the depth of one or more rebars of a reinforced concrete bridge deck as described herein. Other commercial systems may be used, as well, with suitable adaptation, if needed.

The entire contents of U.S. patent application, Ser. No. 09/457,749, entitled DETERMINING THE CONDITION OF A CONCRETE STRUCTURE USING ELECTROMAGNETIC SIGNALS by Roger L. Roberts (the Roberts application), filed on even date herewith, are herein incorporated by reference.

Figure 1:
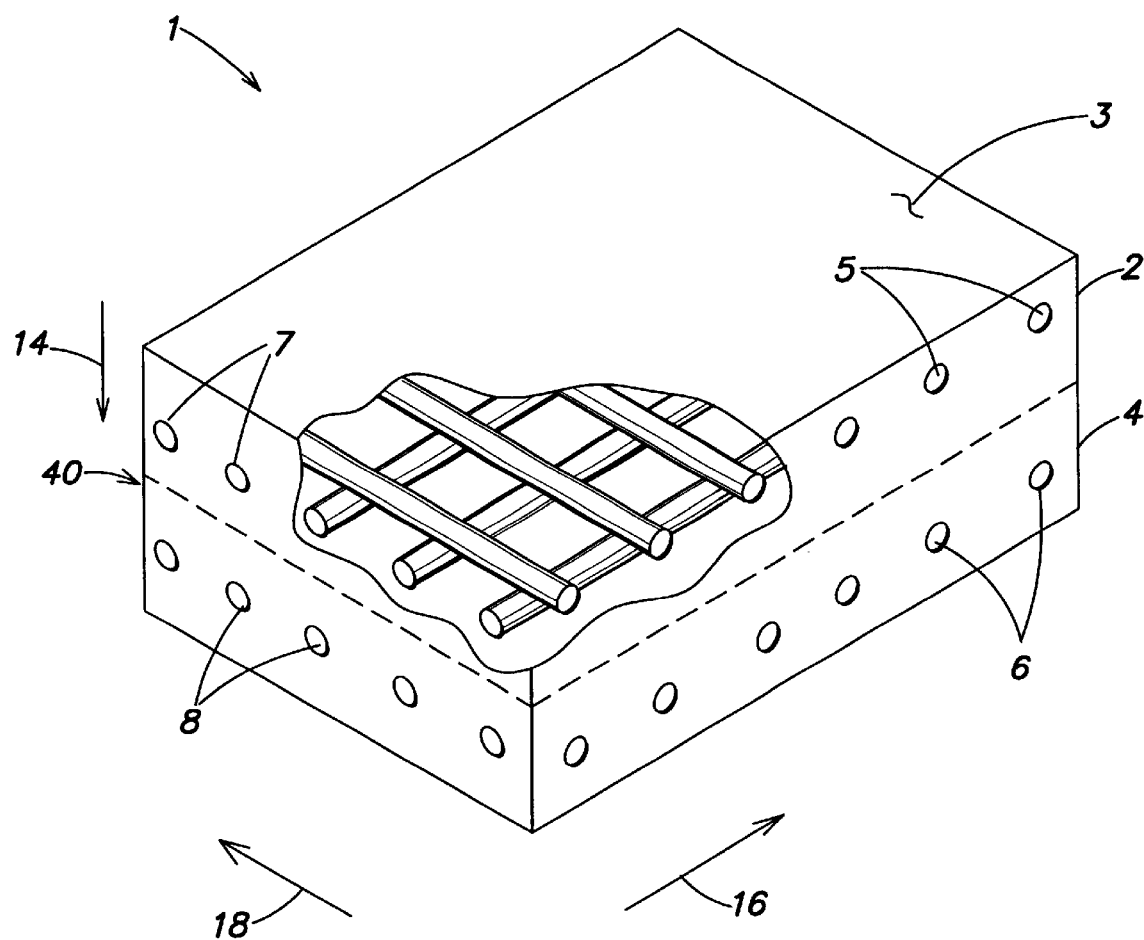
FIG. 1 is a perspective view of an illustrative schematic embodiment of a portion of a reinforced concrete structure, with a partially cut-away, magnified portion.
Figure 2:
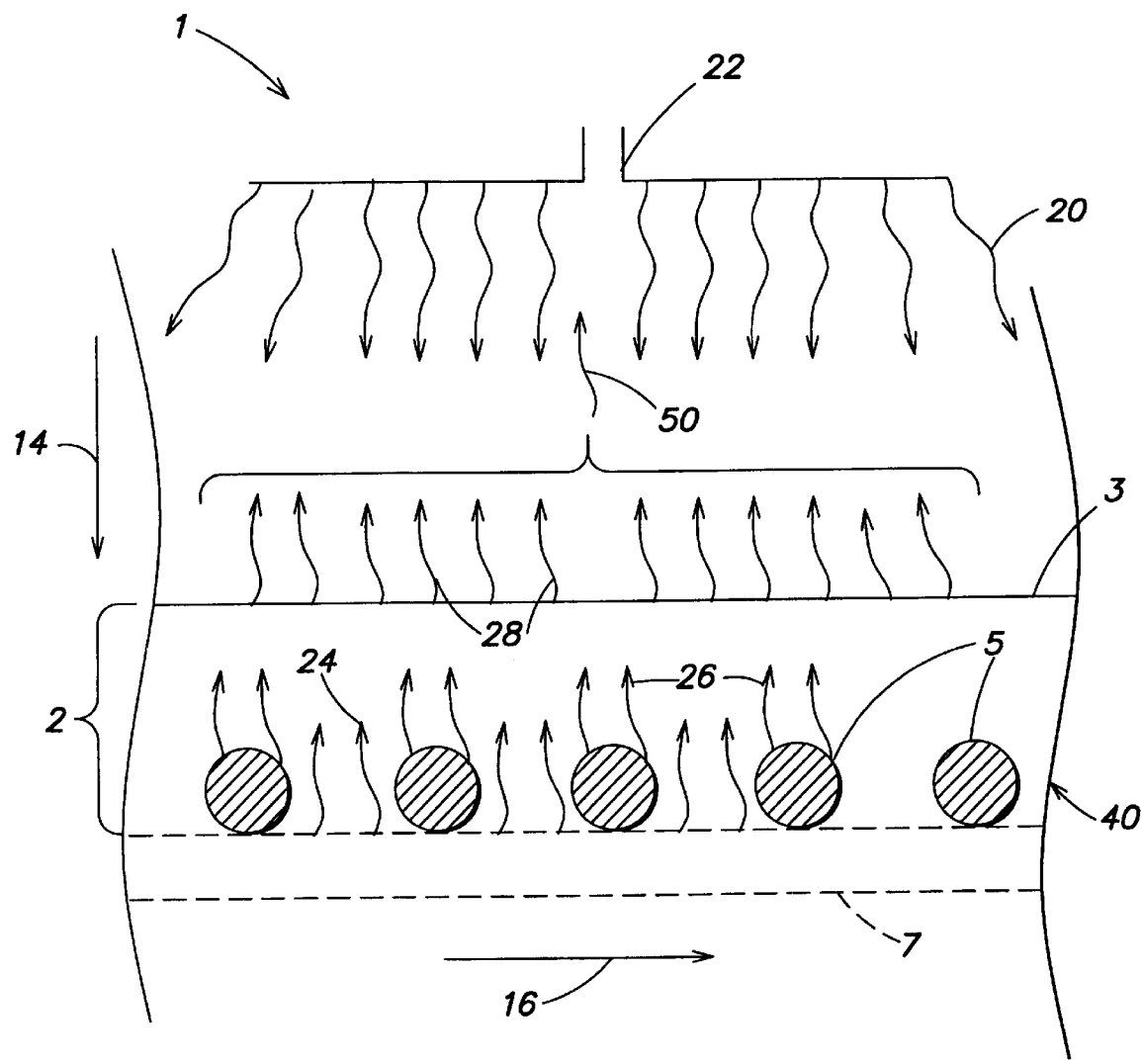
FIG. 2 is a schematic cross-sectional view of an embodiment of a section of a reinforced concrete structure.

FIG. 1 illustrates an example portion of a reinforced concrete bridge deck 1 including a layer 40 of reinforced concrete having a concrete surface 3. FIG. 2 is a cross-sectional view of a portion of the reinforced concrete bridge deck of FIG. 1. For illustrative purposes, the intended path of traffic is indicated by directional indicator 16, which is hereafter also referred to as the longitudinal direction, which corresponds to a length of the bridge deck. Directional indicator 18 indicates a transverse direction corresponding to the width of the bridge deck, and directional indicator 14 indicates a depth corresponding to the thickness of the bridge deck.

Reinforced concrete bridge decks typically contain rebars 5–8 to provide tensile strength. Such rebars 5–8 generally range in diameter from about 0.5 to 1 inch (1.27 to 2.54 centimeters (cm)), typically having a diameter between ⅝ and ¾ inches (1.59 to 1.91 cm). These reinforcement bars typically form two layers 2, 4. The top of the top layer 2 is typically located between about 2 and 7.5 cm below the concrete surface. Due to changes in rebar placement depths over the years, the distance between the top layer 2 and the bottom layer 4 varies, with typical distances ranging from about 1.25 to 4 inches (3.18–10.16 cm) for a typical reinforced bridge deck thickness of 7.5 inches (19 cm). The rebars 5 and 6 that are substantially perpendicular to the travel path on the bridge are referred to herein as transverse bars, and the rebars 7 and 8 substantially parallel to the travel path are referred to herein as longitudinal rebars. Typically, each rebar layer 2 and 4 is comprised of one or more transverse rebars and one or more longitudinal rebars. Top layer 2 includes transverse rebars 5 and longitudinal bars 7, and bottom layer 4 includes transverse bars 6 and longitudinal bars 8.

For illustrative purposes, for each rebar layer 2,4, the transverse rebars 5,6 will be described as being above corresponding longitudinal rebars 7,8, respectively. However, in an alternative embodiment, for each rebar layer 2,4, the longitudinal rebars 7,8 may be above the corresponding transverse rebars 5,6.

Transverse and longitudinal rebars of the same layer are typically affixed together, so that the distance from the top of a transverse rebar 5,6 to the top of a longitudinal rebar 7,8, respectively, is the diameter of the transverse rebar 5,6. Some bridge decks and other concrete structures may have only one layer of rebar, other structures may have rebars aligned in only one direction (for example, transversely or longitudinally), and yet others may have transverse bars located below longitudinal bars.

Rebars of a same layer 2,4 and of a particular alignment such as, for example, transverse 5,6 or longitudinal 7,8, are typically separated by a distance ranging from 10–30 cm.

Ground Penetrating Radar (GPR) provides a tool which may be used in a non-invasive technique for determining the depth of rebars within a concrete structure. High-frequency GPR such as, for example, 1.5 GHz GPR, is particularly well suited for the purpose of locating metallic objects such as, for example, rebars, in concrete.

To accurately calculate the depths to the tops of the transverse rebars 5, using electromagnetic signals, a number of criteria must be met: (1) the vertical resolution of the data collected from the reinforced concrete bridge deck 1 is sufficient to detect small changes in depth, (2) the horizontal resolution of the collected data is sufficient to distinguish between rebars spaced as close as 10 cm apart, (3) the strengths of electromagnetic energy reflected from the rebars is detectable at the receiving antenna, and (4) the propagation velocity of the electromagnetic energy in the concrete is known. Examples of embodiments of how to achieve these criteria are discussed in more detail below.

Determining the depths of one or more rebars in a reinforced concrete bridge deck includes collecting data indicative of the depth of the rebars and analyzing the collected data. Analyzing the data is discussed in more detail below in connection with FIGS. 6 and 7.

Collecting the data may include generating the data by transmitting one or more electromagnetic signals into the reinforced concrete bridge deck, and detecting one or more electromagnetic signals from the bridge deck. Each detected electromagnetic signal 50 may include electromagnetic energy reflected from one or more rebars.

In an embodiment of collecting electromagnetic signals, electromagnetic signals 20 such as, for example, pulses of electromagnetic energy or radar waves, may be transmitted from a transmitting antenna 22 above the bridge. deck surface 3 into the bridge deck 1. For each electromagnetic signal 20 transmitted into the bridge deck 1, a corresponding electromagnetic signal may be detected. When a transmitted electromagnetic signal 20 is propagated through the bridge deck 1, the electromagnetic signal 20 may be reflected by the concrete surface interface 3, producing concrete surface reflections (reflected electromagnetic energy) 28, and the top layer 2 of rebars, producing rebar reflections 24, 26. Thus a detected electromagnetic signal 50 may include concrete surface reflection 28 and rebar reflections 24, 26. Further, in an embodiment using separate antennas to detect and to transmit, the detected electromagnetic signal 50 may also include electromagnetic energy transmitted directly from the transmitting antenna to the receiving antenna, referred to herein as a direct-coupled signal.

These reflections 24, 26 and 28 and the direct-coupled signal may be detected at different times for a given transmitted signal 20, depending on the distance each signal travels and the electrical properties, such as the permittivity, of the mediums through which the signal travels (such as, for example, air and concrete).

In an embodiment, reflections 24, 26 and 28 may then be detected by the transmitting antenna 22. In an alternative embodiment, these reflections 24, 26 and 28 may be received by a receiving antenna proximate to the transmitted antenna 22.

Of the reflections 24, 26 from the top layer 2, the transverse reflections 26 from the transverse rebars 5, which are typically above the longitudinal rebars 7 may be significantly stronger than the longitudinal reflections 24 from the longitudinal rebars 7. To ensure that the transverse reflections 26 are significantly stronger than the longitudinal reflections 24, the transmitted signal. 20 may have a primary electric field polarized in a direction substantially parallel to the transverse rebars 5 and substantially orthogonal to the longitudinal rebars 7.

In an embodiment, the greatest angle between the alignment of any transverse rebar 5 and the primary electrical field polarization is 45°.

Further, transverse reflections 26 are significantly stronger than reflections from rebars 6, 8 of the bottom layer 4 because the transverse rebars 5 are typically over 3 cm closer to the surface of the bridge deck 1 than rebar 6,8 of the bottom layer 4. Consequently, the distance traveled by a transverse reflection 26 is less than the distance traveled by a longitudinal reflection 24. As is well known to those skilled in radar technology, the strength of a radiated electromagnetic signal from a dipole-like antenna, decreases due to geometrical spreading as it travels through a medium. If the medium is concrete, additional signal strength losses are introduced due to conductivity and scattering. Therefore, the added distance traveled by a longitudinal reflection 24 in the concrete layer 40, compared to the distance traveled by the transverse reflection 26 in the concrete layer 40, reduces the strength of the longitudinal reflection 24.

As discussed above, the depth of the transverse rebars 5 of the top rebar layer 2 beneath the concrete surface 3 may be as little as 2 cm. To confidently measure the amplitude of transverse reflections 26 resulting from a single electromagnetic signal 20, the transverse reflections 26 must be capable of being isolated in time from concrete surface reflection 28 and the direct-coupling signal of the detected electromagnetic signal 50. If the transverse reflections 26 are capable of being isolated in time from concrete surface reflection 28 for transverse rebar depth of little as 2 cm, the detected signal may be described as having good vertical resolution.

In an embodiment of collecting data, to be able to isolate transverse reflections 26 from rebars at a depth as shallow as 2 cm, the transmitting antenna, and receiving antenna if different than the transmitting antenna, may be closely coupled to the concrete surface 3. In an optional aspect of this embodiment, the transmitting and receiving antennas are positioned a distance of 0.1 wavelengths of the transmitted signal 20 from the surface 3 of the bridge deck 1. For example, the transmitting and receiving antenna may be placed in a housing having a first side of very small (e.g., 6.6 millimeters) thickness, against that first side.

Figure 4:
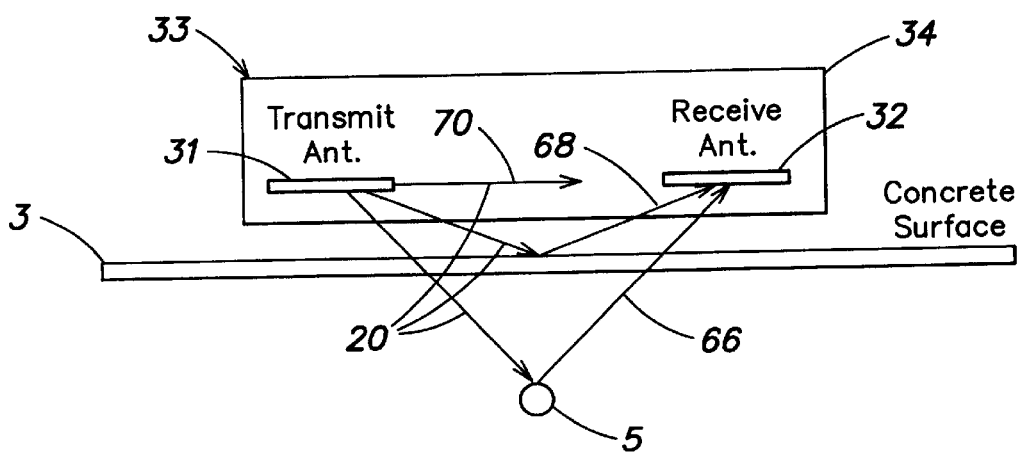
FIG. 4 is a diagram illustrating paths of dominant electromagnetic energy transmitted from a first antenna to a second antenna.

Such a closely-coupled antenna may be referred to herein as a ground-coupled antenna. That first side may be in contact with the enclosed antenna and the surface of the bridge deck 1. FIG. 4 illustrates an embodiment of a ground-coupled antenna unit 33 having an housing 34 and comprising a ground-coupled transmitting antenna 31 such as, for example, a dipole-like antenna, and a ground-coupled receiving antenna 32 such as, for example, a dipole-like antenna. FIG. 4 is discussed in more detail below.

The ground-coupled antenna transmits electromagnetic signals at a center frequency that satisfies two criteria. First, the center frequency is adequate to produce detected electromagnetic signals 50 where the transverse reflections 26 are capable of being distinguished (isolated in time) from the concrete surface reflections 28 (good vertical resolution). Second, the frequency is adequate to provide a transmitted electromagnetic signal strong enough to produce a transverse reflection 26 capable of being detected. In a working embodiment, to satisfy these two criteria, the transmitting antenna 22 may transmit at a center frequency of 1.5.GHz, for example. Typically, electromagnetic waves having a frequency of 1.5 GHz propagate sufficiently well to depths of 15–20 cm in moderately cured concrete.

Figure 3:
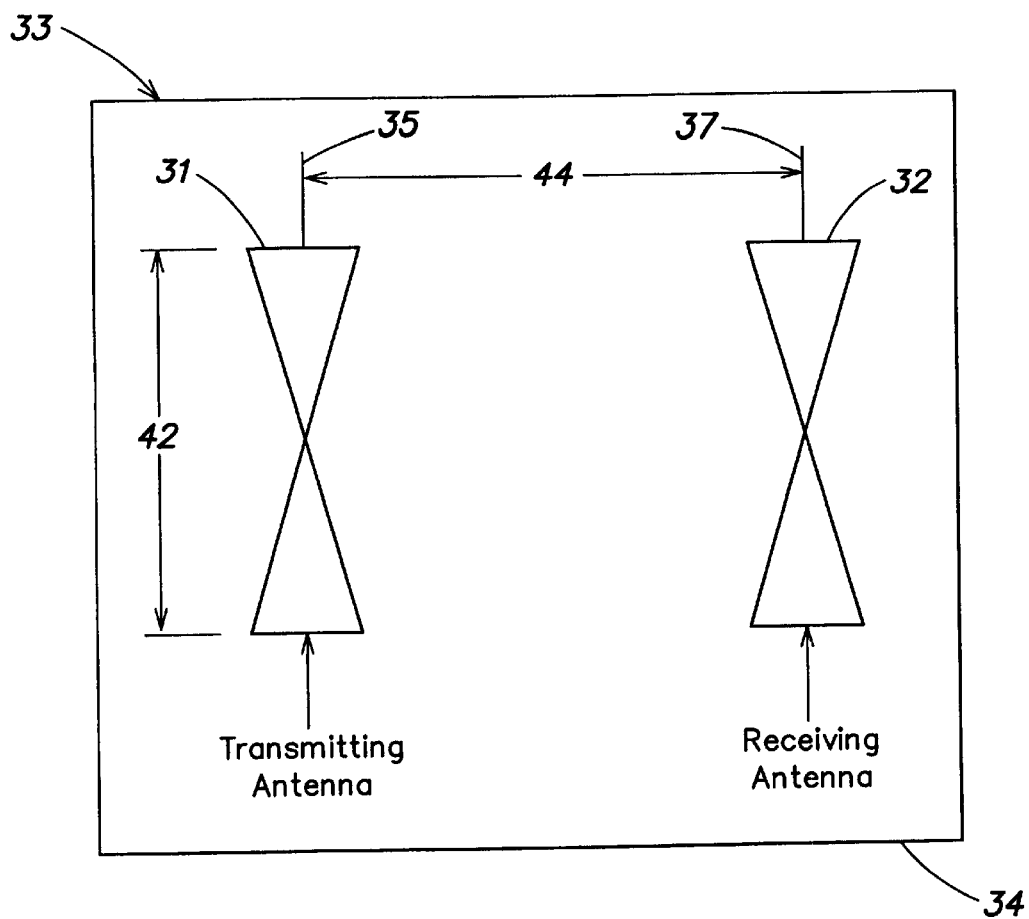
FIG. 3 is a diagram illustrating an embodiment of a configuration of an antenna unit for transmitting and receiving electromagnetic signals.

FIG. 3 is a diagram illustrating an embodiment of an antenna unit 33 having an antenna housing 34 and having a dipole-like transmitting antenna 31 and dipole-like receiving antenna 32, where each antenna has a length 42 of 6 cm to transmit and receive, respectively, electromagnetic signals with a center frequency of at least 1.5 GHz.. A suitable commercial antenna transmitting at a center frequency of 1.5 GHz is the Model 5100 Antenna available from GSSI. Other commercial systems may be used, with suitable adaptation, if needed.

In an embodiment, to further ensure good vertical resolution, the transmitted electromagnetic signal 20 may have a short duration relative to the difference in arrival times of the reflections 24, 26 and 28. Such a short duration lessens the overlap between arrival times of the reflections 24, 26 and 28 to improve vertical resolution. In an optional aspect of this embodiment, the duration of transmission of each electromagnetic signal 20 is approximately the reciprocal of the frequency of the detected signal 50. In an embodiment, the duration of the transmitted electromagnetic signal 20 may be less than a nanosecond such as, for example, approximately 700 picoseconds ($7 \times 10^{-10}$ seconds).

An embodiment of a method of isolating the transverse reflection 26 from a detected electromagnetic signal 50 is described in more detail below in connection to FIGS. 6 and 7.

In an embodiment, a center 35 of the transmitting antenna 31 and a center 37 of the receiving antenna 32 may be spaced a distance 44 adequate to identify individual transverse reflections 26 in a detected signal 50. A detected signal 50 from which individual transverse reflections 26 of transverse rebars 5 separated by a distance as small as 10 cm are capable of being distinguished is said to have good horizontal resolution. In an optional aspect, to identify, in a detected signal 50, individual transverse reflections 26 of transverse rebars 5 separated by as small a distance as 10 cm, the distance 44 between the centers 35,37 of the antennas may be as short as 6 cm.

FIG. 4 illustrates the dominant paths 66, 68 of reflections 26,28, respectively, and the dominant path 70 of the direct-coupling signal between the transmitting and receiving antennas 31,32. The near equal length of the dominant concrete reflection path 68 and the dominant direct-coupling paths for a transmitted electromagnetic signal 20, result in nearly the same arrival time at the receiving antenna 32 by the concrete surface reflection 28 and the direct-coupling signal. The arrival times are so near that the concrete surface reflection 28 and direct-coupling signal may overlap in the detected signal 50. The portion of the detected signal including this overlapping or superposition of the concrete surface reflection and the direct-coupling signal is referred to herein as the direct-coupling portion. The amplitude of the direct-coupling portion may vary in concrete with differing permittivites, however, the arrival time of the peak amplitude of the direct-coupling portion is relatively insensitive to changes in concrete permittivity. This arrival time is referred to hereinafter as time-zero.

The insensitivity of the arrival time of the peak amplitude of the direct-coupled portion of the detected signal 50 provides a reliable time-zero reference. This time-zero reference may be used to determine the propagation time in the concrete of the energy of a transverse reflection 50, which in turn, may be used to determine the depths of one or more rebars, as is described below in more detail below.

Figure 5:
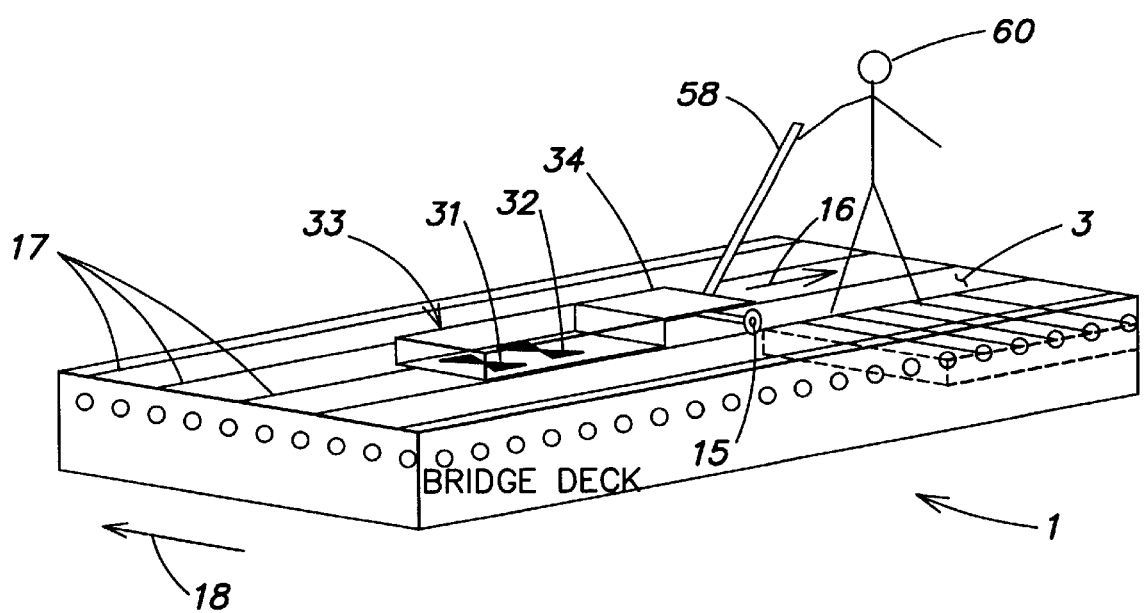
FIG. 5 is a diagram illustrating an embodiment of a method of collecting electromagnetic data from a concrete structure.

In an embodiment of collecting data, a plurality of electromagnetic signals are transmitted and received along one or more data collection paths. FIG. 5 illustrates an embodiment for transmitting and receiving a plurality of electromagnetic signals along one or more data collection paths 17 using ground-coupled antennas 31,32. In an embodiment, data collection paths are approximately parallel. Although collection paths 17 are approximately parallel to the longitudinal direction 16 in FIG. 5, the data may be collected in any direction along the surface of the bridge deck 1 such as, for example, the transverse direction 18.

The point along each collection path 17 at which an electromagnetic signal is transmitted and detected may be referred to herein as a data detection point, and the detected signals 50 at these points may be referred to herein as scans. The scan density (number of scans per unit length) along the collection paths 17 depends on the desired resolution between parallel transverse rebars 5. Further, the scan density chosen may depend on the frequency of the transmitted signal, and the distance from the surface of the bridge deck 1 of the transmitting and receiving antenna.

In an embodiment, where it desired to isolate individual transverse reflections 26 so that individual transverse rebars 5 may be imaged, the transmitting and receiving antennas may be ground-coupled, the transmitted signal may have a center frequency of approximately 1.5 GHz, and a scan density of approximately 40–80 scans/meter may be chosen.

Electromagnetic signals may be collected as shown in FIG. 5, where a ground-coupled antenna unit 33 having an antenna housing 34 and including a transmitting antenna 31 and receiving antenna 32 is moved along one or more collection paths 17 and is closely-coupled to the surface 3 of the bridge deck 1.

In a working embodiment, the antenna unit 33 may be moved manually such as, for example, in FIG. 5, where a ground-coupled antenna unit is pulled by a person 60 using a tow handle 58 or by an animal (e.g. a horse). Alternatively, an antenna unit 33 may be moved by a motorized vehicle.

In an optional embodiment, data may be collected along a plurality of the collection paths 17 contemporaneously. For example, a plurality of antenna units 33 may be moved along parallel collection paths 17 contemporaneously by multiple persons, animals, or motorized vehicles or a single person, animal or motorized vehicle.

Each detected electromagnetic signal 50 may recorded on a recording medium such as a computer-readable medium such as, for example, a magnetic disk or an integrated semiconductor memory. Such data storage devices are discussed in more detail below. For each recorded signal, the location or position of the corresponding detected signal 50 is also recorded. The location may include the position of the detection point along the longitudinal direction 16 of the surface of the bridge deck and the position of the detection point along the transverse direction of the surface of the bridge deck 1.

In an embodiment, the distance along a collection path is determined by recording a starting point of the collection path, and by determining the distance traveled along the collection path from the starting point. This distance may be determined using a distance encoder wheel 15 as shown in FIG. 5 to detect the position of the detection point and to send the position information along with the detected electromagnetic signal 50 to the recording medium.

In an alternative embodiment, the location corresponding to a detection point of a detected electromagnetic signal 50 may be determined by using a global position satellite (GPS) receiver to receive position information from a GPS and send the position information along with the detected signal 50 to the recording medium.

Other known position determination techniques may be used to determine the position of a detection point.

A uniform scan interval along a collection path may be chosen in accordance with the scan density. For example, if the scan density is chosen to be 120 scans/meter, than a scan interval of 0.833 centimeters is chosen. A receiving antenna may be programmed or controlled to detect an electromagnetic signal once every scan interval. To activate detection by a receiving antenna, for each scan interval, the receiving antenna may receive a control signal from a position determination means such as a GPS receiver or distance encoder wheel as discussed above.

Alternatively, to maintain a uniform scan interval, an optical scanning device may be connected to the receiving antenna. A thin strip of material may be laminated to the surface of the bridge deck along an approximately parallel path to the desired collection path. The material may have intermittent reflective and non-reflective surface portions corresponding to the desired scan interval. The optical scanning device may direct a light beam such as, for example, a laser beam, towards the thin strip as the receiving antenna (as well as the entire antenna unit) is moving along the collection path. The scanning device may detect reflections from the thin strip and determine from the reflections when to assert the control signal to activate the receiving antenna. This optical scanning device may be mounted on an adjustable arm extending from the antenna unit or a vehicle moving the antenna unit so that the same thin strip may be used for more than one collection path.

Such an optical scanning technique also may be used to maintain an approximately straight collection path. The optical scanning device could assert a warning signal or inactivate signal when no reflections from the thin strip are detected for a predetermined distance, indicating that the light beam is no longer impacting the thin strip.

Further, such an optical scanning device may also be used to determine the position of the detection points and send the determined position to the recording medium along with the corresponding detected signal 50.

As will be discussed below with respect to the analysis of the electromagnetic signals 50, in order to calculate the depths of one or more rebars in a reinforced concrete bridge deck, the depth of one rebar of known location may be measured. The rebar corresponding to the measured depth may be referred to as the calibration rebar. Such a measurement may be made by drilling a hole through the surface 3 of the bridge deck 1, and mechanically measuring the depth using a measuring device. The location of the calibration rebar must be measured so that its depth can be applied to the propagation time of the energy of transverse reflection 26 associated with the calibration rebar, as will be discussed in more detail below.

Experimental data has revealed that recently-poured concrete on bridge decks can be considered homogeneous in terms of its electrical properties such as, for example, permittivity. Therefore, a constant radar propagation velocity through the concrete can be determined and used to convert rebar reflection arrival times to rebar depths.

Having now described several embodiments for collecting electromagnetic data from a reinforced concrete bridge deck, data analysis of the collected data will now be described.

While the detected electromagnetic signals 50 are being detected, or after some or all of the signals 50 have been detected, the data is then analyzed to determine the depths of one or more transverse rebars in the concrete layer 40 of the reinforced concrete bridge deck 1.

Figure 6:
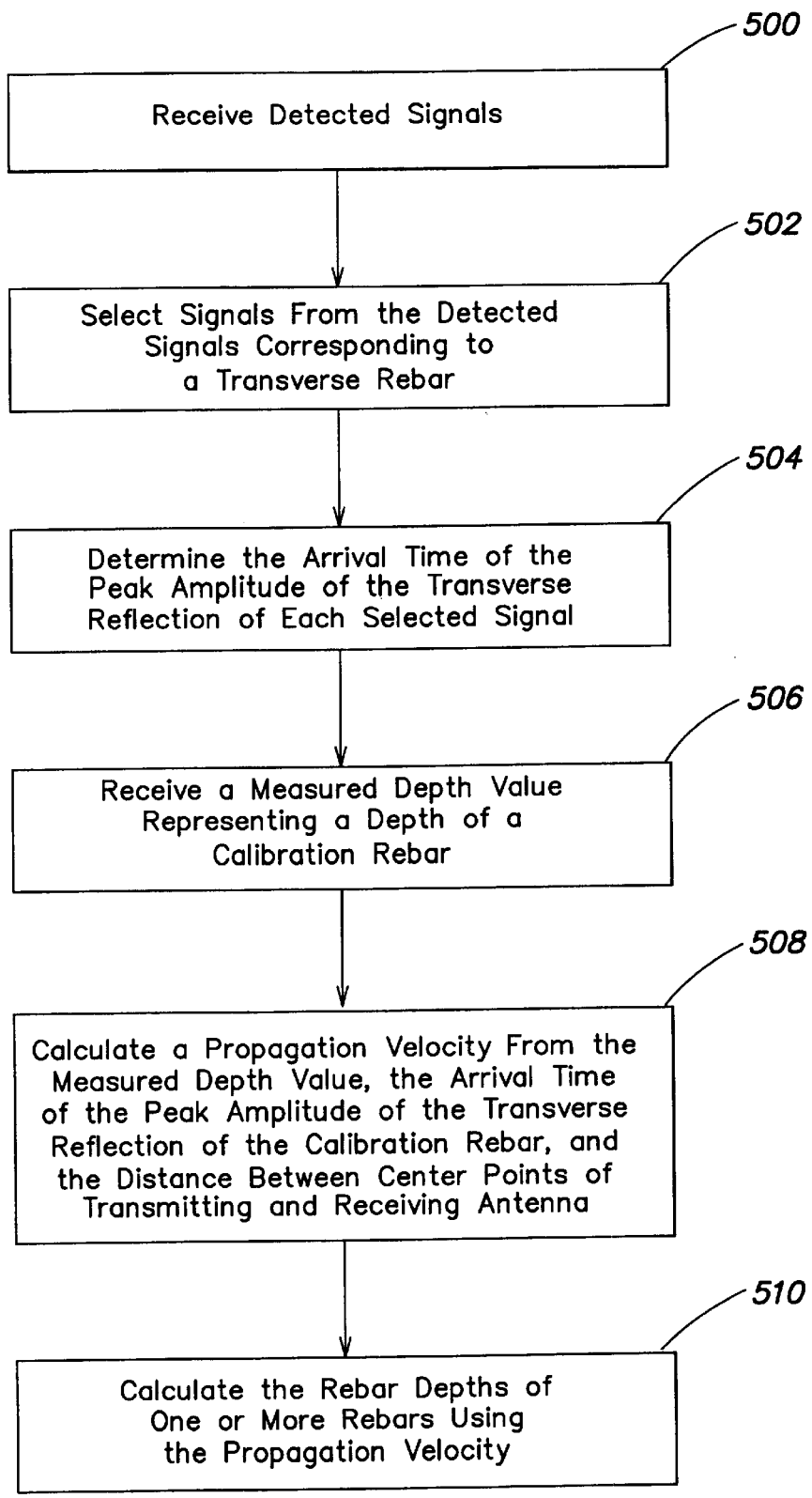
FIG. 6 is a flow chart illustrating an embodiment of a method of analyzing electromagnetic data to determine rebar depths in a concrete structure.

FIG. 6 is a flow chart illustrating an exemplary embodiment of a method for determining the depths of one or more transverse rebars 5 in a concrete reinforced concrete bridge deck 1. (as stated above, if the longitudinal rebars 6 are above the transverse rebars in the top layer 2, then the longitudinal rebars would be the rebars of primary significance). In step 500, the detected signals 50 are received.

Next, in step 502, signals corresponding to the transverse rebars 5 are determined from the detected signals 50. More specifically, it is determined which detected signals 50 were detected at a detection point most directly over a transverse rebar 5. Each of these determined signals may be referred to herein as a data signal corresponding to a transverse rebar 5. An embodiment of determining a signal corresponding to a rebar is described on the Roberts Application in connection with FIG. 7 of the Roberts Application, and is herein incorporated by reference.

A detection point is considered most directly over a transverse rebar 5 when detection is made at a point in time when a midpoint between the transmitting antenna and the receiving antenna is at its closest point along the collection path to a point on the top perimeter of the transverse rebar 5 corresponding to the intersection of a straight line between the center of the transverse rebar 5 and the surface 3 of the concrete deck, the straight line intersecting surface 3 at a right angle.

Each detected signal 50 corresponding to a transverse rebar 5 can be determined by comparing the transverse rebar reflection amplitudes of each signal 50 because the transverse reflection amplitude of a transverse rebar 5 has a highest value when the detection point is most directly over the transverse rebar 5. The amplitude is highest for a detection at this detection point for at least two reasons: (1) at this point, the transverse rebar 5 reflects the most electromagnetic energy of the transmitted signal 20; and (2) at this point, on average, the electromagnetic energy reflected from transverse rebar 5 travels the shortest distance to the receiving antenna, thus losing minimal signal strength due to attenuation.

Figure 7:
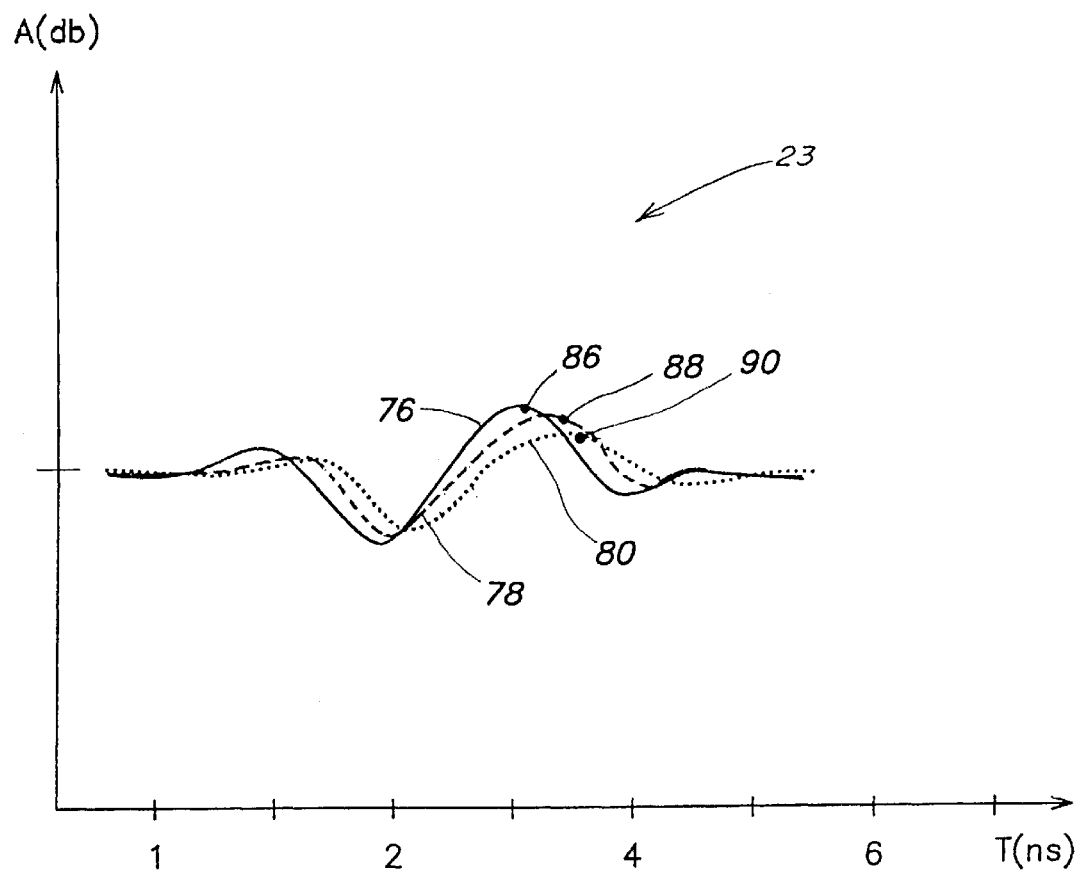
FIG. 7 is a graph illustrating an embodiment of a plurality of electromagnetic data signals detected from a concrete structure.

FIG. 7 is a graph 23 illustrating an embodiment of plotted data signals 76, 78, and 80 representing transverse reflections 26 of detected electromagnetic signals 50. Such reflections may result when the transmitted signals 20 are each a cosine wavelet. The signals are plotted in dB/ns. Signal 76 represents a signal 50 detected at a detection point most directly over a transverse rebar 5. Signal 78 represents a signal 50 detected at a detection point proximate to the detection point corresponding to signal 76. Signal 80 represents a signal 50 detected at a detection point slightly further away from the detection point corresponding to signal 76 than the point corresponding to signal 78. The data signals 76, 78, 80 may represent three consecutive scans along a collection path 17. For the reasons discussed above, signal 76 has a greater transverse reflection amplitude 86 than the transverse reflection amplitude 88 of signal 78, which is greater than the transverse reflection amplitude 90 of signal 80. Furthermore, the arrival time of amplitude 86 is before amplitude 88, whose arrival time is before amplitude 90.

Figure 8:
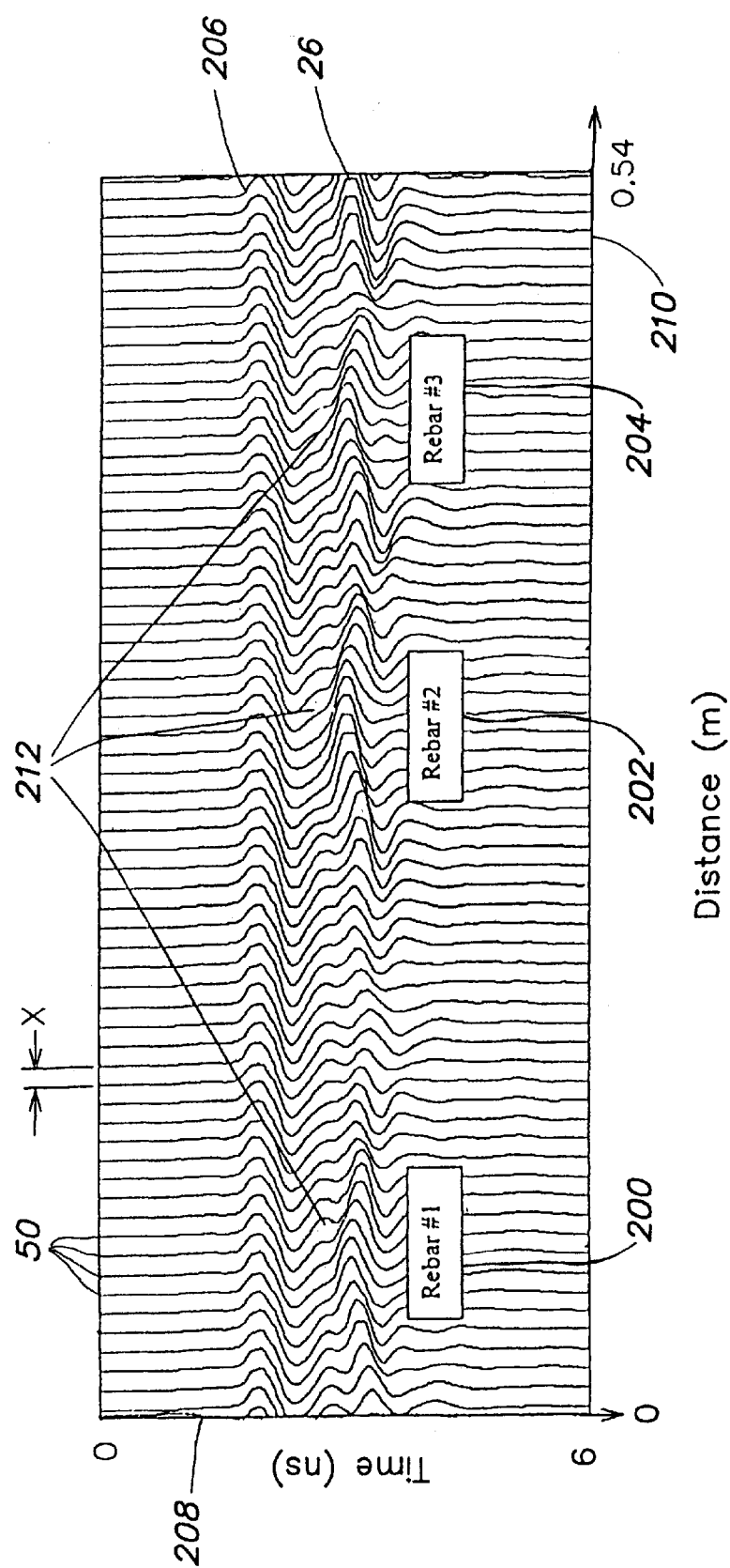
FIG. 8 is a diagram illustrating an embodiment of a graphical representation of the scans of a collection path.

FIG. 8 is a graph illustrating an embodiment of a plurality of detected electromagnetic signals or scans 50 collected along a collection path 17. Such a graph may be referred to herein as a waterfall graph due to the visual impression created by the scans 50. The vertical axis 208 represents time in nanoseconds, and the horizontal axis 210 represents distance along a collection path 17 in meters. This waterfall graph represents a collection of data along a collection path with a scan density of 120 scans/meter, resulting in a scan interval X of 0.83 cm. The positions 200, 202, 204 of three transverse rebars 5 relative to the collection path 17 are superimposed on the waterfall graph. FIG. 8 illustrates the direct-coupling portion 206 and the transverse reflections 26 of each scan 50. Reference 212 indicates the transverse rebar reflections 26 corresponding to scans 50 detected from a detection point most directly over the transverse rebar positions 200, 202, 204. The amplitudes of the direct-coupling portion 206 remain essentially constant relative to the position of the scans relative to the rebar positions 200, 202, 204. The amplitudes of the transverse rebar reflections 26, however, increase as a scan approaches the center of a rebar position 220, 202, 204 for the reasons discussed above.

Returning to FIG. 6, in step 504, the arrival times of the peak amplitudes of the transverse reflection 5 are determined. An embodiment for determining the peak amplitudes of the transverse reflections 26 is described on the Roberts Application in connection with FIG. 7 of the Roberts Application, and is herein incorporated by reference. In an embodiment, the peak amplitudes may be determined visually, by inspecting a visual representation of a scan, wherein the amplitudes of the scan over the detection time (typically 6 ns) may be represented by a numerical value, a distance, a color, or a grayscale value. A user may select from the visual representation the point of the scan with the highest amplitude value for a given time interval corresponding to a transverse reflection amplitude. Each amplitude value along a scan corresponds with an arrival time of the amplitude. Accordingly, when the peak amplitude of the transverse reflection is selected, the arrival time is determined.

The higher the frequency of the transmitted signal 20, the shorter the wavelength of the transmitted signal 20 and the detected signal 50, and consequently, the narrower with respect to time is the duration of the transverse reflection 26. The narrower the transverse reflection, the more accurate is the determined arrival time of the transverse reflection 26. For a typical bridge-deck investigation, the maximum permissible error in determined rebar depth is ±3 mm. Accordingly, in an embodiment, the transmitting antenna is configured to transmit a signal 20 with a center frequency of at least 1.5 GHz. The allowed error of ±3 mm translates to about ±5% of the wavelength of a 1.5 GHz center frequency pulse in concrete.

Next, in steps 506 and 508, the measured depth value of the calibration rebar, discussed above, is received, and the propagation velocity through the concrete layer 40 of the bridge deck is calculated. Due to the homogenous electrical transmission properties of the concrete layer 40, as discussed above, this propagation velocity may be assumed to be constant for each transmitted signals 20, and each transverse reflection 50. The propagation velocity may be determined by applying the following Equation 1:

$$v = \frac{2}{t} \sqrt{(a/2)^2 + d^2} \qquad (1)$$

where:
t propagation time of transverse reflection 26 associated with the calibration rebar inside concrete (ns),
v=propagation velocity inside the concrete (cm/ns),
d=measured depth of calibration rebar (cm), and
a=distance between center point 35 of the transmitting antenna 31 and the center point of the receiving antennas 32 (cm).

In an alternative embodiment, the propagation velocity through the concrete layer 40 is determined by using plane wave propagation theory. The reflection coefficient at the surface 3 of the bridge deck 1 is determined by determining the amplitude of the reflection of a electromagnetic signal from a large metal plate, and dividing this amplitude into the amplitude of the surface reflection 28 to obtain the reflection coefficient at the concrete surface. The reflection coefficient value can then be input into the plane wave reflection coefficient equation calculated based on the velocities of the upper and lower media at a planar interface. Substituting the propagation velocity in air for the upper medium permits solving the equation for the propagation velocity in the lower medium—in this case, concrete.

In another alternative embodiment, the propagation velocity through the concrete layer 40 is determined by migrating said data at multiple velocities and determining which velocity yields the highest resultant transverse reflection amplitude and minimally shifts the rebar reflection arrival time in the data from the data collection points positioned directly above the rebars. The implementation of this technique entails storing the unmigrated scan obtained at the position where the rebar is positioned equidistant from the transmitting and receiving antennas. The data are subsequently migrated at different propagation velocities. At the correct migration velocity, the summation of all of the amplitude values from adjacent scans will theoretically provide the highest peak reflection amplitude in the equidistant scan compared to the peak reflection amplitude in the equidistant scan obtained using other migrated velocities. Furthermore, at the correct migration velocity, the reflection arrival time in the equidistant scan is minimally shifted from the arrival time observed in the unmigrated scan.

In another alternative embodiment, the propagation velocity through the concrete layer 40 is determined by: determining the average values of the direct-coupling portion of the detected signals 50 along the duration of the detection signals 50 to produce an average direct-coupling portion, and determining the highest correlation between the average direct-coupling portion and a library of direct-coupling waveforms determined from concrete with known concrete propagation velocities.

For each selected signal, the propagation time, t, of the transverse reflection may be determined by determining the difference between the arrival time of the peak amplitude of the tranverse reflection 26 and time-zero. Time-zero, discussed above in connection with FIG. 4, is the arrival time of the peak amplitude of the direct-coupled portion of the detected signal 50.

In step 510, the depth of each transverse rebar may then be determined by applying the following Equation 2:

$$x = \frac{1}{2} \sqrt{v^2 y^2 - a^2} \qquad (2)$$

where:
x=where x is the determined depth of the rebar,
y=propagation time of transverse reflection 26 of the signal,
v=propagation velocity inside the concrete (cm/ns), and
a=distance between center point 35 of the transmitting antenna 31 and the center point of the receiving antennas 32 (cm).

As discussed above, it is assumed that the propagation velocity is spatially invariant throughout the portion of the concrete layer 40 of the bridge deck 1 between the surface 3 and the tops of the transverse rebars 5. Experimental data indicates that this assumption is valid within the depth error tolerance of ±3 mm. In an embodiment, this assumption is valid provided the detected signals 50 are obtained from a bridge deck 1 having a concrete layer 40 formed during a single pour. The electromagnetic properties of concrete may change significantly within several weeks following the single pouring as the concrete cures. Consequently, in an embodiment, where adjacent sections of concrete have been poured at least three or more days apart, a different propagation velocity may be determined for each section, and used to calculate the appropriate depths in accordance with the above description.

Figure 9:
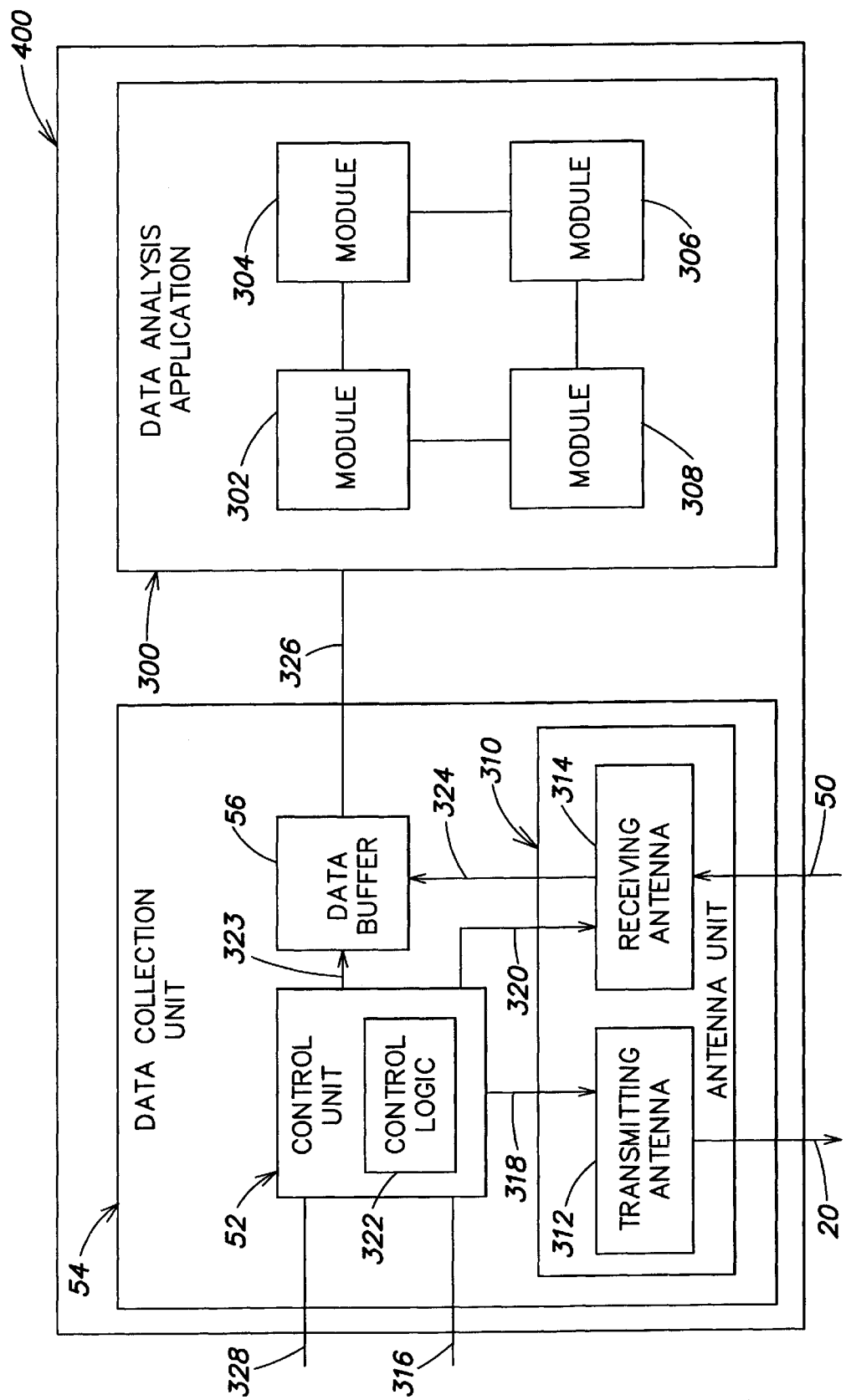
FIG. 9 illustrates an embodiment of a system for determining the depths of one or more rebars from electromagnetic signals detected from a bridge deck.

FIG. 9 illustrates an embodiment of a system 400 for determining the depths of one or more rebars of a concrete bridge deck, including a data collection unit 54 and a data analysis application 300. The data collection unit 54 may include a control unit 52 connected to an antenna unit 310, and a data buffer 56. The antenna unit may include a transmitting antenna 312 that transmits electromagnetic signals 20 and a receiving antenna 314 that detects electromagnetic signals 50.

The control unit 52 may receive a position signal 316 that indicates a position on the surface of a bridge deck 1, or a position along a detection path 17. Such a position signal may be received from a position determination device (not shown) that may determine position using one of the techniques described above or other known techniques. The control unit 52 may contain control logic 322 to assert a first control signal 318 to the transmitting antenna to trigger the receiving antenna 312 to transmit signals 20 depending on the position signal 316, and to assert a second control signal 320 to the receiving antenna 314 antenna to trigger the receiving antenna to detect signals 50 depending on the position signal 316. The control logic 322 may de-assert the control signal 318 to stop the transmitting antenna 312 from transmitting in accordance with the position signal 316, and de-assert the second control signal 320 to stop the receiving antenna 314 from detecting in accordance with the position signal 316.

The receiving antenna 314 may output detected signals 50 on a first signal carrier 324 such as, for example, a wire or a data bus, to the data buffer 56. The data buffer 56 may be a recording medium as discussed above, and particularly may be a computer-readable storage medium of a variety of types discussed below. The data buffer 56 may temporarily store a plurality of detected signals 50, the number of stored signals depending on the capacity of the data buffer 56 and other well-known efficiency considerations. For example, the data buffer may store an entire collection path 17 of detected signals 50.

The data collection unit 54 may also include an analog-to-digital converter (A/D converter) to convert the analog detected signals 50 to digital signals before being stored in the data buffer 56 or before being sent to the data analysis application 300. Alternatively, the A/D converter may be part of a computer system accessed by the data analysis application 300, examples of which are discussed below in more detail.

The control unit 52 may have a second input 328 to receive data collection parameters.

Such parameters may include: the duration of each transmitted signal 20, the scan interval, the duration of each detected signal 50, the number of scans per collection path 17 (or the length of the collection path 17), the number of bits to use in the data buffer 56 to store a given value if the data buffer 56 is a digital recording medium, and various parameters for the control of the antennas. Such parameters may be programmed into the control unit 54 or may be received from a user input device such as described below.

The data collection unit 54 may also include an analog-to-digital converter (A/D converter) to convert the analog detected signals 50 to digital signals before being stored in the data buffer 56 or before being sent to the data analysis application 300. Alternatively, the AID converter may be part of a computer system accessed by the data analysis application 300, examples of which are discussed below in more detail.

The data analysis unit may include a plurality of interconnected modules 302–308 to implement the processing steps described above in connection with FIG. 6.

The data analysis application 300 may be implemented with a typical computer system. The invention is not limited to any specific computer described herein. Many other different machines may be used to implement the data analysis module. Such a suitable computer system includes a processing unit which performs a variety of functions and a manner well-known in the art, in response to instructions provided from an application program. The processing unit functions according to a program known as the operating system, of which many types are known in the art. The steps of an application program are typically provided in random access memory (RAM) in machine-readable form because programs are typically stored on a non-volatile memory, such as a hard disk or floppy disk. After a user selects an application program, it is loaded from the hard disk to the RAM, and the processing unit proceeds through the sequence of instructions of the application program.

The computer system also includes a user input/output (I/O) interface. The user interface typically includes a display apparatus (not shown), such as a cathode-ray-tube (CRT) display in an input device (not shown), such as a keyboard or mouse. A variety of other known input and output devices may be used, such as speech generation and recognition units, audio output devices, etc.

The computer system also includes a video and audio data I/O subsystem. Such a subsystem is well-known in the art and the present invention is not limited to the specific subsystem described herein. The audio portion of the subsystem includes an analog-to-digital (A/D) converter (not shown), which receives analog audio information and converts it to digital information. The digital information may be compressed using known compression systems, for storage on the hard disk to use at another time. A typical video portion of the subsystem includes a video image compressor/decompressor (not shown) of which many are known in the art. Such compressor/decompressors converts analog video information into compressed digital information. The compressed digital information may be stored on a hard disk for use at a later time.

One or more output devices may be connected to the computer system implementing the data analysis application 300. Example output devices include a cathode ray tube (CRT) display, liquid crystal displays (LCD) and other video output devices, printers, communication devices such as a modem, storage devices such as disk or tape, and audio output. One or more input devices may be connected to the computer system. Examplary input devices include a keyboard, keypad, track ball, mouse, pen and tablet, communication device, and data input devices such as audio and video capture devices and sensors. The computer system is not limited to the particular input or output devices used in combination with the computer system or to those described herein.

The data analysis application 300 may be implemented on a general purpose computer system which is programmable using a computer programming language, such as "C++," JAVA or other language, such as a scripting language or even assembly language. The computer system may also be specially programmed, special purpose hardware. In a general purpose computer system, the processor is typically a commercially available processor, such as the series x86 and Pentium processors, available from Iritel, similar devices from AMD and Cyrix, the 680X0 series microprocessors available from Motorola, and the PowerPC microprocessor from IBM. Many other processors are available. Such a microprocessor executes a program called an operating system, of which WindowsNT, Windows95 or 98, UNIX, Linux, DOS, VMS, MacOS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, for example, a floppy disk or a read/write CD, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the invention is not limited thereto. The invention is not limited to a particular memory system.

Such a system may be implemented in software or hardware or firmware, or a combination of the three. The various elements of the system, either individually or in combination may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The data analysis application 300 is not limited to a particular computer platform, particular processor, or particular programming language. Additionally, the computer system may be a multi processor computer system or may include multiple computers connected over a computer network. Each of the processing steps of FIG. 6 may be separate modules of a computer program, or may be separate computer programs or a combination thereof. Such modules may be operable on separate computers.

Having now described some illustrative embodiments, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method steps or apparatus elements, it should be understood that those steps and those elements may be combined in other ways to accomplish the same objectives. Steps, elements and features discussed only in connection with one embodiment are not intended to be excluded from a similar role in other embodiments.

What is claim is:

1. A method of determining, for a substantially concrete structure having at least a first side and containing at least a first reinforcing bar, a distance of the first reinforcing bar from the first side of the substantially concrete structure, the method comprising:

receiving a plurality of computer-readable data signals, wherein each data signal represents an electromagnetic signal detected from an area of the concrete structure, and wherein one or more of the detected electromagnetic signals include electromagnetic energy reflected from the concrete structure as a result of a corresponding electromagnetic signal transmitted into the concrete structure;

selecting one of the data signals, the selected data signal corresponding to the first reinforcing bar; and determining a first distance of the first reinforcing bar from the first side of the substantially concrete structure based on the selected data signal alone from among the plurality of data signals.

2. The method of claim 1, wherein the first reinforcing bar has a longitudinal axis aligned along a first dimension, and a plurality of electromagnetic signals have been transmitted into the substantially concrete structure at different locations along a second dimension approximately orthogonal to the first dimension, and wherein the selected data signal includes electromagnetic energy reflected from the first reinforcing bar as a result of the transmission of one of the plurality of electromagnetic signals.

3. The method of claim 1, wherein each detected electromagnetic signal is detected at a different location on the first side.

4. The method of claim 3, wherein each transmitted electromagnetic signal corresponding to one of the detected electromagnetic signals is transmitted at a different location on the first side.

5. The method of claim 1, further comprising:

detecting each detected electromagnetic signal with a same receiver; and transmitting each corresponding electromagnetic signal with a same transmitter.

6. The method of claim 1, further comprising:

temporarily storing the data signals before selecting one of the data signals.

7. The method of claim 1, wherein the selected data signal represents an electromagnetic signal detected over a detection period of time, and wherein determining the first distance includes:

determining a portion of the selected data signal during which the detected electromagnetic signal, represented by the selected data signal, includes electromagnetic energy reflected from the first reinforcing bar; and determining, from the determined portion of the selected data signal, the first distance of the first reinforcing bar from the first side.

8. The method of claim 7, further comprising:

determining a velocity value representing a velocity at which an electromagnetic signal propagates in concrete of the substantially concrete structure, wherein determining the first distance includes:

determining a first point in time during the detection period corresponding to a peak amplitude of the electromagnetic energy reflected from the first reinforcing bar; and calculating the first distance using the velocity value and the first point in time.

9. The method of claim 8, wherein the detected electromagnetic signal represented by the selected data signal includes a direct-coupled portion, and the step of determining the first distance further includes:

subtracting the first point in time from a second point in time to produce a propagation time within the concrete structure for the detected electromagnetic signal represented by the selected data signal, wherein the second point in time corresponds to a peak amplitude of the direct-coupled portion; and calculating the first distance using the velocity value and the propagation time.

10. The method of claim 9, wherein the transmitted electromagnetic signals are transmitted from a first antenna and the detected electromagnetic signals are detected by a second antenna located a second distance from the first antenna, wherein the step of calculating the first distance includes:

applying an equation:

$$d = \frac{1}{2}\sqrt{v^2 t^2 - a^2},$$

wherein d is the first distance, t is the propagation time, v is the velocity value, and a is the second distance.

11. The method of claim 8, wherein determining the first distance includes:

receiving a distance value indicative of a distance measured from the first side of the concrete structure to a second reinforcing bar contained in the substantially concrete structure; and calculating the velocity value from the distance value.

12. The method of claim 11, wherein the transmitted electromagnetic signals are transmitted from a first antenna and the detected electromagnetic signals are detected by a second antenna located a second distance from the first antenna, wherein determining the first distance includes:

determining a propagation time within the substantially concrete structure of an electromagnetic signal transmitted into the substantially concrete structure from the first side, reflected from the second reinforcing bar and detected at the first side, wherein the velocity value is calculated by applying an equation:

$$v = \frac{2}{t}\sqrt{(a/2)^2 + d^2},$$

wherein v is the velocity value, a is the second distance, t is the propagation time and d is the distance value.

13. The method of claim 7, wherein each transmitted electromagnetic signal is transmitted at a different position along the first side of the concrete structure, and the method further comprises:

for each data signal, determining a portion of the data signal during which the detected electromagnetic signal represented by the data signal includes electromagnetic energy reflected from the first reinforcing bar; and for each data signal, determining a peak amplitude of the data signal during the determined portion, wherein selecting one of the data signals includes selecting the selected data signal for having a peak amplitude of a highest magnitude from among the data signals corresponding to electromagnetic signals transmitted within a spatial interval of a first length along the first side of the substantially concrete structure.

14. The method of claim 13, further comprising:

migrating the data signals to facilitate determining that the selected data signal has a peak amplitude of the highest magnitude.

15. The method of claim 1, wherein the transmitted electromagnetic signals are transmitted from a first antenna and the detected electromagnetic signals are detected by a second antenna located a second distance from the first antenna, the second distance having a midpoint on an imaginary straight line between the first and second antennas, and wherein an amplitude of each data signal is directly related to a distance between the area corresponding to the data signal and the midpoint of the second distance.

16. The method of claim 1, wherein each of the data signals represents an electromagnetic signal detected at a point along a substantially straight line along a first dimension of the first side of the concrete structure, and each detected electromagnetic signal is detected over a period of time, the method further comprising:

displaying a graph of one or more of the data signals, a first axis of the graph representing time of detection, a second axis of the graph representing a distance along the first dimension, the displaying including representing an amplitude of each of the one or more data signals over the detection time, wherein a location, with respect to the second axis, of each represented data signal corresponds to a point at which the signal was detected.

17. The method of claim 16, wherein the step of selecting the data signal includes:

selecting the data signal from the graph in accordance with the amplitudes of the represented data signals.

18. The method of claim 1, wherein the method further comprises:

adjusting the selected data signal by removing from the selected data signal data representing electromagnetic signals not reflected from the substantially concrete structure; and determining the first distance from the adjusted data signal.

19. For a substantially concrete structure having at least a first side and containing at least a first reinforcing bar, a system for determining a distance of the first reinforcing bar from the first side of the substantially concrete structure, the system comprising:

means for receiving a plurality of computer-readable data signals, wherein each data signal represents an electromagnetic signal detected from an area within the concrete structure, and wherein one or more of the detected electromagnetic signals include electromagnetic energy reflected from the concrete structure as a result of a corresponding electromagnetic signal transmitted into the concrete structure;

means for selecting one of the data signals, the selected data signal corresponding to the first reinforcing bar; and means for determining a first distance of the corresponding reinforcing bar from the first side of the substantially concrete structure based on the selected data signal alone from among the plurality of data signals.

20. The system of claim 19, wherein the first reinforcing bar has a longitudinal axis aligned along a first dimension, and a plurality of electromagnetic signals have been transmitted into the substantially concrete structure at different locations along a second dimension approximately orthogonal to the first dimension, and wherein the selected data signal includes electromagnetic energy reflected from the first reinforcing bar as a result of the transmission of one of the plurality of electromagnetic signals.

21. The system of claim 19, wherein each detected electromagnetic signal is detected at a different location on the first side.

22. The system of claim 21, wherein each transmitted electromagnetic signal corresponding to one of the detected electromagnetic signals is transmitted at a different location on the first side.

23. The system of claim 19, further comprising:

a receiver to detect each of the detected electromagnetic signals; and a transmitter to transmit each of the corresponding transmitted electromagnetic signals.

24. The system of claim 19, further comprising:
a data buffer to temporarily store the data signals before selecting one of the data signals.

25. The system of claim 19, the selected data signal represents an electromagnetic signal detected over a detection period of time, and wherein the means for determining the first distance includes:
means for determining a portion of the selected data signal during which the detected electromagnetic signal, represented by the selected data signal, includes electromagnetic energy reflected from the first reinforcing bar; and
means for determining the first distance of the first reinforcing bar from the first side from the determined portion of the selected data signal.

26. The system of claim 25, further comprising:
means for determining a velocity value representing a velocity at which an electromagnetic signal propagates in concrete of the substantially concrete structure, and
wherein the means for determining the first distance includes:
means for determining a first point in time during the detection period corresponding to a peak amplitude of the electromagnetic energy reflected from the first reinforcing bar; and
means for calculating the first distance using the velocity value and the first point in time.

27. The system of claim 26, wherein, the detected electromagnetic signal corresponding to the selected data signal includes a direct-coupled portion and the means for determining the first distance further includes:
means for subtracting the first point in time from a second point in time to produce a propagation time within the concrete structure for the detected electromagnetic signal represented by the selected data signal, wherein the second point in time corresponds to a peak amplitude of the direct-coupled portion; and
means for calculating the first distance using the velocity value and the propagation time.

28. The system of claim 27, wherein the transmitted electromagnetic signals are transmitted from a first antenna and the detected electromagnetic signals are detected by a second antenna located a second distance from the first antenna, wherein the means for calculating the first distance includes:
means for applying an equation:

$$d = \frac{1}{2}\sqrt{v^2 t^2 - a^2},$$

wherein d is the first distance, t is the propagation time, v is the velocity value, and a is the second distance.

29. The system of claim 26, wherein the means for determining the first distance includes:
means for receiving a distance value indicative of a distance measured from the first side of the concrete structure to a second reinforcing bar contained in the substantially concrete structure; and
means for calculating the velocity value from the distance value.

30. The system of claim 29, wherein the transmitted electromagnetic signals are transmitted from a first antenna and the detected electromagnetic signals are detected by a second antenna located a second distance from the first antenna, wherein the means for determining the first distance includes:
means for determining a propagation time within the substantially concrete structure of an electromagnetic signal transmitted into the substantially concrete structure from the first side, reflected from the second reinforcing bar and detected at the first side,
wherein the means for calculating the velocity value includes means for applying an equation:

$$v = \frac{2}{t}\sqrt{(a/2)^2 + d^2},$$

wherein v is the velocity value, a is the second distance, t is the propagation time and d is the distance value.

31. The system of claim 25, wherein each transmitted electromagnetic signal was transmitted at a different position along the first side of the concrete structure, and the system further comprises:
means for determining, for each data signal, a portion of the data signal during which the detected electromagnetic signal represented by the data signal includes electromagnetic energy reflected from the first reinforcing bar; and
means for determining, for each data signal, a peak amplitude of the data signal during the determined portion,
wherein the means for selecting one of the data signals includes, for a spatial interval of a first length along the first side of the substantially concrete structure, means for selecting the selected data signal for having a peak amplitude of a highest magnitude from among the data signals corresponding to electromagnetic signals transmitted within the spatial interval.

32. The system of claim 25, wherein each transmitted electromagnetic signal was transmitted at a different position along the first side of the concrete structure, and the system further comprises:
means for determining, for each data signal, a portion of the data signal during which the detected electromagnetic signal represented by the data signal includes electromagnetic energy reflected from the first reinforcing bar; and
means for determining, for each data signal, a peak amplitude of the data signal during the determined portion,
wherein the means for selecting one of the data signals includes, for a spatial interval of a first length along the first side of the substantially concrete structure, means for selecting the selected data signal for having a peak amplitude of a highest magnitude from among the data signals corresponding to electromagnetic signals transmitted within the spatial interval.

33. The system of claim 19, wherein the transmitted electromagnetic signals were transmitted from a first antenna and the detected electromagnetic signals were detected by a second antenna located a second distance from the first antenna, the second distance having a midpoint on an imaginary straight between the first and second antennas, and wherein an amplitude of each data signal is directly related to a distance between the area corresponding to the data signal and the midpoint of the second distance.

34. The system of claim 19, wherein each of the data signals represent an electromagnetic signal detected at a point along a substantially straight line along a first dimension of the first side of the concrete structure, and each detected electromagnetic signal is detected over a period of time, the system further comprising:

means for displaying a graph of one or more of the data signals, a first axis of the graph representing time of detection, a second axis of the graph representing a distance along the first dimension, the means for displaying including means for representing an amplitude of each of the one or more data signals over the detection time, wherein a location, with respect to the second axis, of each represented data signal corresponds to a point at which the signal was detected.

35. The system of claim 19, wherein the means for selecting the data signal includes:

means for selecting the data signal from the graph in accordance with an amplitude of the detected electromagnetic signal represented by the selected data signal.

36. The method of claim 19, wherein the system further comprises:

means for adjusting the selected data signal by removing from the selected data signal data representing electromagnetic signals not reflected from the substantially concrete structure; and means for determining the first distance from the adjusted data signal.

37. For a substantially concrete structure having at least a first side and containing at least a first reinforcing bar, a system for determining a distance of the first reinforcing bar from the first side of the substantially concrete structure, the system comprising:

a computer-readable storage medium to store a plurality of computer-readable data signals, wherein each data signal represents an electromagnetic signal detected from the concrete structure, and one or more of the detected electromagnetic signals include electromagnetic energy reflected from the concrete structure as a result of a corresponding electromagnetic signal transmitted into the concrete structure, and wherein each detected signal corresponds to an area within the concrete structure; and a data analysis application including:

a first selection module to receive the data signals, to select one of the data signals, the selected data signal corresponding to the first reinforcing bar, and to output the selected data signal; and a first distance determination module to receive the selected data signal, to determine a first distance of the first reinforcing bar from the first side of the substantially concrete structure based on the selected data signal alone from among the plurality of data signals, and to output the determined first distance.

38. The system of claim 37, wherein the first reinforcing bar has a longitudinal axis aligned along a first dimension, and a plurality of electromagnetic signals have been transmitted into the substantially concrete structure at different locations along a second dimension approximately orthogonal to the first dimension, and wherein the selected data signal includes electromagnetic energy reflected from the first reinforcing bar as a result of the transmission of- one of the plurality of electromagnetic signals.

39. The system of claim 37, wherein each detected electromagnetic signal is detected at a different location on the first side.

40. The system of claim 39, wherein each transmitted electromagnetic signal corresponding to one of the detected electromagnetic signals is transmitted at a different location on the first side.

41. The system of claim 37, further comprising:

a receiver to detect each of the detected electromagnetic signals; and a transmitter to transmit each of the corresponding transmitted electromagnetic signals.

42. The system of claim 37, further comprising:

a data buffer to temporarily store the data signals before selecting one of the data signals.

43. The system of claim 37, wherein the selected data signal represents an electromagnetic signal detected over a detection period of time, and wherein the first distance determination module includes:

a signal portion determination module to receive the selected data signal, determine a portion of the selected signal during which the detected electromagnetic signal, represented by the selected data signal, includes electromagnetic energy reflected from the first reinforcing bar, and output the determined portion, wherein the first distance of the first reinforcing bar from the first side is determined from the determined portion of the selected data signal.

44. The system of claim 43, further comprising:

a velocity determination module to determine a velocity value representing a velocity at which an electromagnetic signal propagates in concrete of the substantially concrete structure, and wherein the first distance determination module includes:

a first time determination module to receive the selected data signal determine for the selected signal a first point in time during the detection period corresponding to a peak amplitude of the electromagnetic energy reflected from the first reinforcing bar, and output the first point in time; and a first distance calculation module to receive the velocity value and the first point in time, calculate the first distance based on the velocity value and the first point in time, and output the calculated first distance.

45. The system of claim 44, wherein the detected electromagnetic signal represented by the selected data signal includes a direct-coupled portion, and the first distance determination further includes:

a subtraction module to receive the first point in time and a second point in time, subtract the first point in time from the second point in time to produce a propagation time within the concrete structure for the detected electromagnetic signal represented by the selected data signal, and output the propagation time, wherein the second point in time corresponds to a peak amplitude of the direct-coupled portion, and wherein the first distance determination module receives the propagation time and calculates the first distance using the velocity value and the propagation time.

46. The system of claim 45, wherein the transmitted electromagnetic signals are transmitted from a first antenna and the detected electromagnetic signals are detected by a second antenna located a second distance from the first antenna, wherein the first distance calculation module includes:

means for applying an equation:

$$d = \frac{1}{2}\sqrt{v^2 t^2 - a^2},$$

wherein d is the first distance, t is the propagation time, v is the velocity value, and a is the second distance.

47. The system of claim 44, wherein the velocity determination module receives a distance value indicative of a distance measured from the first side of the concrete structure to a second reinforcing bar contained in the substantially concrete structure, and calculates the velocity value from the distance value.

48. The system of claim 47, wherein the transmitted electromagnetic signals were transmitted from a first antenna and the detected electromagnetic signals were detected by a second antenna located a second distance from the first antenna, wherein the first distance determination module includes:

a propagation time determination module to determine a propagation time within the substantially concrete structure of an electromagnetic signal transmitted into the substantially concrete structure from the first side, reflected from the second reinforcing bar and detected at the first side, wherein the velocity determination module includes means for applying an equation:

$$d = \frac{1}{2}\sqrt{v^2 t^2 - a^2},$$

wherein v is the velocity value, a is the second distance, t is the propagation time and d is the distance value.

49. The system of claim 43, wherein each transmitted electromagnetic signal was transmitted at a different position along the first side of the concrete structure, and wherein the signal portion determination module is further operative to receive each data signal, to determine, for each data signal, a portion of the data signal during which the detected electromagnetic signal represented by the data signal includes electromagnetic energy reflected from the first reinforcing bar and to output the determined portions, and the system further comprises:

a peak amplitude determination module to receive the data signals, determine a peak amplitude for each data signal during the determined portion, and output the peak amplitudes, wherein the first selection module, for a spatial interval of a first length along the first side of the substantially concrete structure, selects the selected data signal for having a peak amplitude of a highest magnitude from among the data signals corresponding to electromagnetic signals transmitted within the spatial interval.

50. The system of claim 46, further comprising:

a migration module to receive the data signals, migrate the data signals to facilitate determining that the selected data signal has a peak amplitude of the highest magnitude, and output the migrated data signals.

51. The system of claim 37, wherein the transmitted electromagnetic signals are transmitted from a first antenna and the detected electromagnetic signals are detected by a second antenna located a second distance from the first antenna, the second distance having a midpoint on an imaginary straight between the first and second antennas, and wherein an amplitude of each data signal is directly related to a distance between the area corresponding to the data signal and the midpoint of the second distance.

52. The system of claim 37, wherein each of the data signals represent an electromagnetic signal detected at a point along a substantially straight line along a first dimension of the first side of the concrete structure, and each detected electromagnetic signal is detected over a period of time, the system further comprising:

a display device to display a graph of one or more of the data signals, a first axis of the graph representing time of detection, a second axis of the graph representing a distance along the first dimension, the displaying including representing an amplitude of each of the one or more data signals over the detection time, wherein a location, with respect to the second axis, of each represented data signal corresponds to a point at which the signal was detected.

53. The system of claim 52, wherein the data analysis application further includes:

a graphical user interface to permit a user to select the selected data signal from the graph in accordance with the amplitudes of the represented data signals.

54. The system of claim 37, wherein the data analysis application further includes:

a data adjustment module to receive the selected data signal, adjust the selected data signal by removing from the selected data signal data representing electromagnetic signals not reflected from the substantially concrete structure, and output the adjusted data signal, wherein the first distance is determined from the adjusted data signal.

55. A method of determining a distance of an electromagnetically-reflective object from a first side of a structure containing the object, wherein a plurality of electromagnetic signals have been transmitted into the structure, each transmitted electromagnetic signal transmitted at a different location on the first side, and a plurality of electromagnetic signals have been detected from the structure, each detected electromagnetic signal detected at a different location and corresponding to a respective one of the transmitted electromagnetic signals, wherein one or more of the detected electromagnetic signals include electromagnetic energy reflected from the object as a result of the transmitted electromagnetic signal corresponding to the detected electromagnetic signal, the method comprising:

receiving a plurality of data signals, each data signal representing a respective one of the detected electromagnetic signals;

selecting one of the data signals; and determining a distance of the object from the first side of the structure based on the selected data signal alone from among the plurality of data signals.

56. The method of claim 55, wherein the first reinforcing bar has a longitudinal axis aligned along a first dimension, and the plurality of electromagnetic signals have been transmitted into the structure at different locations along a second dimension approximately orthogonal to the first dimension.

57. The method of claim 55, wherein selecting includes selecting based on a peak amplitude of the detected electromagnetic signal, represented by the selected data signal, resulting from electromagnetic energy reflected from the object.

58. The method of claim 57, the structure is a substantially concrete structure.

59. The method of claim 58, wherein the one or more objects are reinforcing bars.

60. The method of claim 57, wherein the one or more objects are reinforcing bars.

61. The method of claim 55, wherein the structure is a substantially concrete structure.

62. The method of claim 61, wherein the one or more objects are reinforcing bars.

63. The method of claim 55, wherein the one or more objects are reinforcing bars.

64. The method of claim 55, further comprising:
detecting each detected electromagnetic signal with a same receiver; and transmitting each corresponding electromagnetic signal with a same transmitter.

65. The method of claim 55, further comprising:
temporarily storing the data signals before selecting one of the data signals.

66. A system for determining a distance of an electromagnetically-reflective object from a first side of a structure containing the object, wherein a plurality of electromagnetic signals have been transmitted into the structure, each transmitted electromagnetic signal transmitted at a different location on the first side, and a plurality of electromagnetic signals have been detected from the structure, each detected electromagnetic signal detected at a different location on the first side and corresponding to a respective one of the transmitted electromagnetic signals, wherein one or more of the detected electromagnetic signals include electromagnetic energy reflected from the object as a result of the transmitted electromagnetic signal corresponding to the detected electromagnetic signal, the system comprising:
one or more inputs to receive a plurality of data signals, each data signals representing a respective one of the detected electromagnetic signals;
means for selecting one of the data signals; and
means for determining a distance of the object from the first side of the structure based on the selected data signal alone from among the plurality of data signals.

67. The system of claim 66, wherein the first reinforcing bar has a longitudinal axis aligned along a first dimension, and the plurality of electromagnetic signals have been transmitted into the structure at different locations along a second dimension approximately orthogonal to the first dimension.

68. The system of claim 66, wherein the means for selecting includes means for selecting based on a peak amplitude of the detected electromagnetic signal, represented by the selected data signal resulting from electromagnetic energy reflected from the object.

69. The system of claim 68, wherein the structure is a substantially concrete structure.

70. The system of claim 69, wherein the structure is a substantially concrete structure.

71. The system of claim 68, wherein the one or more objects are reinforcing bars.

72. The system of claim 66, wherein the structure is a substantially concrete structure.

73. The system of claim 72, wherein the structure is a substantially concrete structure.

74. The system of claim 66, wherein the one or more objects are reinforcing bars.

75. The system of claim 66, further comprising:
a receiver to detect each of the detected electromagnetic signals; and
a transmitter to transmit each of the corresponding transmitted electromagnetic signals.

76. The system of claim 66, further comprising:
a data buffer to temporarily store the data signals before selecting one of the data signals.

77. A computer program product, comprising:
a computer-readable medium; and
computer-readable signals stored on the computer-readable medium that define instructions that, as a result of being executed by a computer, instruct the computer to perform a process of determining a distance of an electromagnetically-reflective object from a first side of a structure containing the object, wherein a plurality of electromagnetic signals have been transmitted into the structure, each transmitted electromagnetic signal transmitted at a different location on the first side, and a plurality of electromagnetic signals have been detected from the structure, each detected electromagnetic signal detected at a different location on the first side and corresponding to a respective one of the transmitted electromagnetic signals, wherein one or more of the detected electromagnetic signals include electromagnetic energy reflected from the object as a result of the transmitted electromagnetic signal corresponding to the detected electromagnetic signal, the process comprising:
receiving a plurality of data signals, each data signals representing a respective one of the detected electromagnetic signals;
selecting one of the data signals; and
determining a distance of the object from the first side of the structure based on the selected data signal alone from among the plurality of data signals.

78. The computer-readable medium of claim 77, wherein the first reinforcing bar has a longitudinal axis aligned along a first dimension, and the plurality of electromagnetic signals have been transmitted into the structure at different locations along a second dimension approximately orthogonal to the first dimension.

79. The computer program product of claim 77, wherein selecting includes selecting based on a peak amplitude of the detected electromagnetic signal, represented by the selected data signal, resulting from electromagnetic energy reflected from the object.

80. The computer program product of claim 79, wherein the structure is a substantially concrete structure.

81. The computer program product of claim 80, wherein the one or more objects are reinforcing bars.

82. The computer program product of claim 79, wherein the one or more objects are reinforcing bars.

83. The computer program product of claim 77, wherein the structure is a substantially concrete structure.

84. The computer program product of claim 83, wherein the one or more objects are reinforcing bars.

85. The computer program product of claim 77, wherein the one or more objects are reinforcing bars.

86. The computer program product of claim 77, wherein the process further comprises:
detecting each detecte d electromagnetic signal with a same receiver; and
transmitting each corresponding electromagnetic signal with a same transmitter.

87. The computer program product of claim 77, wherein the process further comprises:
temporarily storing the data signals before selecting one of the data signals.

* * * * *